United States Patent
Browne et al.

(10) Patent No.: US 9,057,046 B2
(45) Date of Patent: Jun. 16, 2015

(54) CASSETTE CONTAINING GROWTH MEDIUM

(75) Inventors: Douglas Browne, Groton, MA (US); Don Straus, Cambridge, MA (US); Chad Mace, Hudson, NH (US)

(73) Assignee: Rapid Micro Biosystems, Inc., Lowell, MA (US)

( * ) Notice: Subject to any disclaimer, the term of this patent is extended or adjusted under 35 U.S.C. 154(b) by 2082 days.

(21) Appl. No.: 11/527,196

(22) Filed: Sep. 26, 2006

(65) Prior Publication Data
US 2007/0212747 A1   Sep. 13, 2007

Related U.S. Application Data

(60) Provisional application No. 60/720,683, filed on Sep. 26, 2005.

(51) Int. Cl.
*C12M 1/34* (2006.01)
*C12M 1/22* (2006.01)
*C12M 1/00* (2006.01)
*C12M 1/12* (2006.01)

(52) U.S. Cl.
CPC ............ *C12M 23/22* (2013.01); *C12M 25/02* (2013.01)

(58) Field of Classification Search
CPC ...... C12M 23/10; C12M 25/02; C12M 25/04; C12M 41/36
USPC ......... 435/288.3, 288.7, 297.2, 297.5, 305.1, 435/305.4
See application file for complete search history.

(56) References Cited

U.S. PATENT DOCUMENTS

| | | | |
|---|---|---|---|
| 2,672,431 A * | 3/1954 | Goetz | 435/287.7 |
| 2,761,813 A | 9/1956 | Goetz | |
| 3,694,317 A | 9/1972 | Scher | |
| 3,981,776 A | 9/1976 | Saxholm | |
| 4,097,586 A | 6/1978 | Gross | |
| 4,098,876 A | 7/1978 | Piasio et al. | |
| 4,115,535 A | 9/1978 | Giaever | |
| 4,125,375 A | 11/1978 | Hunter | |
| 4,129,419 A | 12/1978 | Hermann, Jr. | |

(Continued)

FOREIGN PATENT DOCUMENTS

| | | |
|---|---|---|
| AU | 760425 B2 | 3/2000 |
| CN | 101254482 A | 9/2008 |

(Continued)

OTHER PUBLICATIONS

English Language machine translation of JP 11-346795 (Dec. 21, 1999).*

(Continued)

*Primary Examiner* — William H Beisner
(74) *Attorney, Agent, or Firm* — Clark & Elbing LLP

(57) ABSTRACT

The invention features devices for capturing and culturing cells (e.g., microorganisms, cells containing microorganisms, or cells from eukaryotic cell cultures) and methods of using these devices. One device is a cassette containing growth media that may be employed in an automated rapid enumeration system. The cassette has, for example, been enhanced with features for controlling surface flatness, optical imaging, controlled dehydration of semi solid nutrient media, controlled air and particle exchange, and automated handling. Another device of the invention is a filtration funnel that may used to concentrate cells in a sample onto a membrane.

36 Claims, 15 Drawing Sheets

(56) References Cited

U.S. PATENT DOCUMENTS

| | | | |
|---|---|---|---|
| 4,141,687 | A | 2/1979 | Forrest et al. |
| 4,157,323 | A | 6/1979 | Yen et al. |
| 4,177,253 | A | 12/1979 | Davies et al. |
| 4,222,744 | A | 9/1980 | McConnell |
| 4,436,826 | A | 3/1984 | Wang |
| 4,438,068 | A | 3/1984 | Forrest |
| 4,454,233 | A | 6/1984 | Wang |
| 4,455,370 | A | 6/1984 | Bartelsman et al. |
| 4,477,578 | A | 10/1984 | Miles et al. |
| 4,537,861 | A | 8/1985 | Elings et al. |
| 4,562,157 | A | 12/1985 | Lowe et al. |
| 4,565,783 | A | 1/1986 | Hansen et al. |
| 4,582,810 | A | 4/1986 | Rosenstein et al. |
| 4,587,213 | A | 5/1986 | Malecki |
| 4,614,585 | A | 9/1986 | Mehra et al. |
| 4,693,972 | A | 9/1987 | Mansour et al. |
| 4,731,337 | A | 3/1988 | Luotola et al. |
| 4,745,077 | A | 5/1988 | Holian et al. |
| 4,777,137 | A | 10/1988 | Lemonnier |
| 4,777,145 | A | 10/1988 | Luotola et al. |
| 4,912,037 | A | 3/1990 | Lemonnier et al. |
| 4,922,092 | A | 5/1990 | Rushbrooke et al. |
| 4,959,301 | A | 9/1990 | Weaver et al. |
| 4,988,302 | A * | 1/1991 | Smith et al. ............... 435/288.3 |
| 4,988,618 | A | 1/1991 | Li et al. |
| 5,073,497 | A | 12/1991 | Schwartz |
| 5,089,413 | A | 2/1992 | Nelson et al. |
| 5,137,812 | A | 8/1992 | Matner |
| 5,190,666 | A | 3/1993 | Bisconte |
| 5,232,838 | A | 8/1993 | Nelson et al. |
| 5,238,810 | A | 8/1993 | Fujiwara et al. |
| 5,258,284 | A | 11/1993 | Moris, Jr. et al. |
| 5,262,526 | A | 11/1993 | Sasamoto et al. |
| 5,292,644 | A | 3/1994 | Berg |
| 5,306,420 | A | 4/1994 | Bisconte |
| 5,321,545 | A | 6/1994 | Bisconte |
| 5,355,215 | A | 10/1994 | Schroeder et al. |
| 5,366,867 | A | 11/1994 | Kawakami et al. |
| 5,464,749 | A | 11/1995 | Schwarzberg et al. |
| 5,474,910 | A | 12/1995 | Alfano |
| 5,510,246 | A | 4/1996 | Morgan |
| 5,538,857 | A | 7/1996 | Rosenthal et al. |
| 5,541,069 | A | 7/1996 | Mortensen et al. |
| 5,552,272 | A | 9/1996 | Bogart |
| 5,558,839 | A | 9/1996 | Matte et al. |
| 5,582,982 | A | 12/1996 | Cubbage et al. |
| 5,585,241 | A | 12/1996 | Lindmo |
| 5,604,351 | A | 2/1997 | Bisconte |
| 5,606,413 | A | 2/1997 | Bellus et al. |
| 5,624,850 | A | 4/1997 | Kumar et al. |
| 5,653,939 | A | 8/1997 | Hollis et al. |
| 5,663,057 | A | 9/1997 | Drocourt et al. |
| 5,672,880 | A | 9/1997 | Kain |
| 5,681,530 | A | 10/1997 | Kuster et al. |
| 5,681,712 | A | 10/1997 | Nelson |
| 5,694,478 | A | 12/1997 | Braier et al. |
| 5,705,402 | A | 1/1998 | Leland et al. |
| 5,736,405 | A | 4/1998 | Alfano et al. |
| 5,744,322 | A | 4/1998 | Krejcarek et al. |
| 5,766,868 | A | 6/1998 | Seto |
| 5,792,617 | A | 8/1998 | Rotman |
| 5,814,454 | A | 9/1998 | Ju |
| 5,821,066 | A | 10/1998 | Pyle |
| 5,828,716 | A | 10/1998 | Bisconte de Saint Julien |
| 5,843,766 | A | 12/1998 | Applegate et al. |
| 5,852,498 | A | 12/1998 | Youvan et al. |
| 5,861,270 | A | 1/1999 | Nelis |
| 5,891,394 | A | 4/1999 | Drocourt et al. |
| 5,914,245 | A | 6/1999 | Bylina et al. |
| 5,958,790 | A | 9/1999 | Cerny |
| 5,968,766 | A | 10/1999 | Powers |
| 5,976,892 | A | 11/1999 | Bisconte |
| 5,981,180 | A | 11/1999 | Chandler et al. |
| 5,985,675 | A | 11/1999 | Charm et al. |
| 5,993,740 | A | 11/1999 | Niiyama et al. |
| 6,048,723 | A | 4/2000 | Banes |
| 6,051,395 | A | 4/2000 | Rocco |
| 6,121,055 | A | 9/2000 | Hargreaves |
| 6,122,396 | A | 9/2000 | King et al. |
| 6,130,931 | A | 10/2000 | Laurila et al. |
| 6,140,653 | A | 10/2000 | Che |
| 6,165,742 | A | 12/2000 | Ofjord et al. |
| 6,171,780 | B1 | 1/2001 | Pham et al. |
| 6,200,762 | B1 | 3/2001 | Zlokarnik et al. |
| 6,214,560 | B1 | 4/2001 | Yguerabide et al. |
| 6,258,326 | B1 * | 7/2001 | Modlin ..................... 422/102 |
| 6,259,807 | B1 | 7/2001 | Ravkin |
| 6,268,222 | B1 | 7/2001 | Chandler et al. |
| 6,274,384 | B1 | 8/2001 | Starzl et al. |
| 6,306,589 | B1 | 10/2001 | Muller et al. |
| 6,309,822 | B1 | 10/2001 | Fodor et al. |
| 6,345,115 | B1 | 2/2002 | Ramm et al. |
| 6,358,730 | B1 * | 3/2002 | Kane ..................... 435/297.5 |
| 6,472,166 | B1 | 10/2002 | Wardlaw et al. |
| 6,582,912 | B1 | 6/2003 | Rousseau et al. |
| 6,623,983 | B1 | 9/2003 | Terstappen et al. |
| 6,664,528 | B1 | 12/2003 | Cartlidge et al. |
| 6,710,879 | B1 | 3/2004 | Hansen et al. |
| 6,727,071 | B1 | 4/2004 | Dunlay et al. |
| 6,764,648 | B1 | 7/2004 | Roach et al. |
| 6,852,527 | B2 | 2/2005 | Chan et al. |
| 6,919,960 | B2 | 7/2005 | Hansen et al. |
| 7,068,365 | B2 | 6/2006 | Hansen et al. |
| 7,160,687 | B1 | 1/2007 | Kapur et al. |
| 7,582,415 | B2 | 9/2009 | Straus |
| 7,763,405 | B2 | 7/2010 | Wu et al. |
| 7,820,430 | B2 | 10/2010 | Weng et al. |
| 2001/0039060 | A1 | 11/2001 | Siiman et al. |
| 2002/0028471 | A1 | 3/2002 | Oberhardt |
| 2002/0055092 | A1 | 5/2002 | Hochman |
| 2002/0137106 | A1 | 9/2002 | Leung et al. |
| 2003/0082516 | A1 | 5/2003 | Straus |
| 2003/0143580 | A1 | 7/2003 | Straus |
| 2003/0170613 | A1 | 9/2003 | Straus |
| 2004/0048395 | A1 | 3/2004 | Lee et al. |
| 2004/0171121 | A1 | 9/2004 | Leppla et al. |
| 2004/0172000 | A1 | 9/2004 | Roe et al. |
| 2004/0246483 | A1 | 12/2004 | Hansen et al. |
| 2005/0013737 | A1 | 1/2005 | Chow et al. |
| 2005/0148085 | A1 | 7/2005 | Larsen |
| 2005/0191687 | A1 | 9/2005 | Wang et al. |
| 2005/0220670 | A1 | 10/2005 | Palmieri et al. |
| 2005/0221403 | A1 | 10/2005 | Gazenko |
| 2005/0225766 | A1 | 10/2005 | Hansen et al. |
| 2005/0226779 | A1 * | 10/2005 | Oldham et al. ................. 422/99 |
| 2006/0006067 | A1 | 1/2006 | Unger |
| 2006/0051816 | A1 | 3/2006 | Hsieh et al. |
| 2006/0121055 | A1 | 6/2006 | Campbell et al. |
| 2006/0129327 | A1 | 6/2006 | Kim et al. |
| 2006/0188967 | A1 | 8/2006 | Nalin et al. |
| 2006/0210435 | A1 | 9/2006 | Alavie et al. |
| 2006/0216696 | A1 | 9/2006 | Goguen |
| 2006/0256340 | A1 | 11/2006 | Hansen et al. |
| 2006/0292552 | A1 | 12/2006 | Haquette et al. |
| 2007/0014695 | A1 | 1/2007 | Yue et al. |
| 2007/0184546 | A1 | 8/2007 | Farrelly et al. |
| 2007/0212681 | A1 | 9/2007 | Shapiro et al. |
| 2008/0003571 | A1 | 1/2008 | McKernan et al. |
| 2008/0014576 | A1 | 1/2008 | Jovanovich et al. |
| 2008/0032328 | A1 | 2/2008 | Cline et al. |
| 2008/0038738 | A1 | 2/2008 | Weigum et al. |
| 2008/0200343 | A1 | 8/2008 | Clemens et al. |
| 2008/0206099 | A1 | 8/2008 | Aruga et al. |
| 2009/0315987 | A1 | 12/2009 | Straus |
| 2010/0248281 | A1 | 9/2010 | Straus |
| 2012/0045826 | A1 | 2/2012 | Yantz et al. |
| 2012/0046203 | A1 | 2/2012 | Walsh et al. |
| 2012/0149007 | A1 | 6/2012 | Abrams et al. |
| 2013/0011566 | A1 | 1/2013 | Colin et al. |

FOREIGN PATENT DOCUMENTS

| | | |
|---|---|---|
| DE | 19608320 A1 | 8/1997 |
| DE | 19631997 | 2/1998 |

(56) References Cited

FOREIGN PATENT DOCUMENTS

| | | |
|---|---|---|
| DE | 19940810 A1 | 5/2000 |
| EP | 171174 A2 * | 2/1986 |
| EP | 0574977 | 12/1993 |
| EP | 0753732 A2 | 1/1997 |
| EP | 1207394 | 5/2002 |
| EP | 1508374 A2 | 2/2005 |
| EP | 1432786 B1 | 7/2009 |
| JP | S62-501647 A | 7/1987 |
| JP | H02-502405 A | 8/1990 |
| JP | 03083598 A * | 4/1991 |
| JP | 3102240 A | 4/1991 |
| JP | 10-295362 | 11/1998 |
| JP | 11346795 A * | 12/1999 |
| JP | 2000-509827 | 8/2000 |
| JP | 2001-224355 | 8/2001 |
| JP | 2001-512875 | 8/2001 |
| JP | 2002-125656 | 5/2002 |
| JP | 2003-294596 A | 10/2003 |
| JP | 2006-087336 A | 4/2006 |
| JP | 2006-162466 A | 6/2006 |
| JP | 2007-526807 A | 9/2007 |
| JP | 2008-513022 A | 5/2008 |
| JP | 2009-513111 A | 4/2009 |
| WO | WO 8301581 A1 * | 5/1983 |
| WO | WO-86/04684 A1 | 8/1986 |
| WO | WO-89/05456 A1 | 6/1989 |
| WO | WO-97/40181 A1 | 10/1997 |
| WO | WO 97/44664 | 11/1997 |
| WO | WO 98/38490 | 9/1998 |
| WO | WO 98/50577 | 11/1998 |
| WO | WO 99/08233 | 2/1999 |
| WO | WO 99/20789 | 4/1999 |
| WO | WO 99/35483 | 7/1999 |
| WO | WO 99/36577 | 7/1999 |
| WO | WO 99/58948 | 11/1999 |
| WO | WO 00/04382 | 1/2000 |
| WO | WO 00/47766 | 8/2000 |
| WO | WO 01/57522 | 8/2001 |
| WO | WO 01/61348 | 8/2001 |
| WO | WO 03/022999 | 3/2003 |
| WO | WO 03/036290 | 5/2003 |
| WO | WO 03/073817 | 9/2003 |
| WO | WO-2005/082254 A2 | 9/2005 |
| WO | WO-2006/032044 A2 | 3/2006 |
| WO | WO-2008/005998 A2 | 1/2008 |
| WO | WO-2011/117545 A1 | 9/2011 |
| WO | WO-2013/070730 A2 | 5/2013 |
| WO | WO-2013/158666 A1 | 10/2013 |

OTHER PUBLICATIONS

Al-Hakiem et al., "Development of Fluoroimmunassays for the Determination of Individual or Combined Levels of Procainamide and N-Acetylprocainamide in Serum." *J. Immunoassay* 3(1):91-110 (1982).
Allman et al., "Fluoroimmunoassay of Progesterone in Human Serum or Plasma" *Clin. Chem.* 27(7):1176-1179 (1981).
Anonymous, The Brain, Enchanted Learning.com, http://www.enchantedlearning.com/subjects/anatomy/brain.neuron.html, copyright 2001-2007, printed Nov. 4, 2007, pp. 1-4.
Clean Technology, vol. 5, p. 60-61 (1995) [in Japanese].
Colony Counter (http://www.topac.com/acolyte.html), downloaded Apr. 12, 2005, p. 1-3.
Colony Counter Models and Specifications (http://biologics-inc.com/cc-models.htm), downloaded Apr. 15, 2005, p. 1-3.
Corkidi et al., "COVASIAM: An Image Analysis Method That Allows Detection of Confluent Microbial Colonies and Colonies of Various Sizes for Automated Counting," *Appl. Environ. Microbiol.* 64(4):1400-1404 (1998).
Definition and Procedure for the Determination of the Method Detection Limit, Appendix B to 40 C.F.R. § 136, available at http://access.gpo.gov (retrieved Nov. 20, 2007), pp. 343-346.
Digital Multi-Purpose High-Resolution Colony and Plaque Counter (http://www.loats.com/mla.html), downloaded Apr. 12, 2005, p. 1-3.
Esteban et al., "Improved Direct Epifluorescent Filter Technique for Rapid Bioburden Control in Intravenous Solutions," *J. Parenter. Sci. Technol.* 46:146-149 (1992).
Frost, "Improved Technic for the Micro or Little Plate Method of Counting Bacteria in Milk," p. 176-184 (1920).
"Innovative Plate Holder for Colony Counter," Downloaded from http://www.laboratorytalk.com on Oct. 16, 2002 (2 pages).
"Innovative Plate Holder for ProtoCOL," Downloaded from http://www.synbiosis.com on Oct. 16, 2002 (2 pages).
Kamentsky, "Laser Scanning Cytometry," In *Cytometry*, Z. Darzynkiewicz, H. Crissman, and J. Robinsnon, Eds., San Diego, Academic Press, pp. 51-87 (2001).
Lamture et al., "Direct Detection of Nucleic Acid Hybridization on the Surface of a Charge Coupled Device," *Nucleic Acids Res.* 22(11):2121-5 (1994).
Loats et al., "LAI High-Resolution Automated Copy Colony Counting System—Mouse Lymphoma Assay: Performance Analysis," (http://loats.com/docs/HRCCval/HRCCval/HRCCval/HRCCval.html), p. 1-11 (1990).
Logtenberg et al., "Enumeration of (Auto)Antibody Producing Cells in Human Using the 'Spot-ELISA,'" *Immunol. Lett.* 9:343-347 (1985).
Masuko et al., "A Novel Method for Detection and Counting of Single Bacteria in a Wide Field Using an Ultra-High-Sensitivity TV Camera Without a Microscope," *FEMS Microbiol. Lett.* 81:287-290 (1991).
Masuko et al., "Rapid Detection and Counting of Single Bacteria in a Wide Field Using a Photon-Counting TV Camera," *FEMS Microbiol. Lett.* 83:231-238 (1991).
Mignon-Godefroy et al., "Solid Phase Cytometry for Detection of Rare Events," *Cytometry* 27:336-344 (1997).
Miraglia, "Homogeneous Cell-and Bead-Based Assays for High Throughput Screening Using Fluorometric Microvolume Assay Technology," *J. Biomol. Screening* 4:193-204 (1999).
Nargessi et al., "Magnetizable Solid-Phase Fluoroimmunoassay of Thyroxine by a Sequential Addition Technique." *Clin Chem* 26(12):1701-1703 (1980).
Nargessi et al., "Immunoassays for Serum C-reactive Protein Employing Fluorophore-Labelled Reactants." *J. Immunol. Methods* 71(1):17-24 (1984).
PerkinElmer, Inc., GeneScreen™ Hybridization Transfer Membranes, Application Notes, available at http://las.perkinelmer.com/, retrieved Feb. 27, 2007.
Rousseau, "New Miniaturized Highly Sensitive Immunoassay Device for Quantitative Measurement of Soluble or Particular Antigen or Antibodies in a Liquid Sample," *Clin. Chem.* 45(9):1685-1687 (1999).
Schultz, "Single Target Molecule Detection with Nonbleaching Multicolor Optical Immunolabels," *Proc. Natl. Acad. Sci. U.S.A.* 97(3):996-1001 (2000).
Sorcerer Automated Colony Counting, Perceptive Instruments, 2 pages, 2002.
Susa et al., "*Legionella pneumophila* Infection in Intratracheally Inoculated T Cell-Depleted or -Nondepleted A/J Mice," *J. Immunol.* 160:316-321 (1998).
System Specifications (http://www.loats.com/order_info.html), p. 1-7 (1999).
Technical Specification (http://www.perceptive.co.uk/products/scc/techspec.html), downloaded Apr. 12, 2005, p. 1-2.
Thomas et al., "Making Gold Nanoparticles Glow: Enhanced Emission from a Surface-Bound Fluoroprobe," *J. Am. Chem. Soc.* 122:2655-2656 (2000).
Tibbe, "Optical Tracking and Detection of Immunomagnetically Selected and Aligned Cells," *Nature Biotechnol.* 17:1210-1213 (1999).
Viinikka et al., "A Two-Site Immunofluorometric Assay for Human Placental Lactogen," *Clin. Chim. Acta* 114(1):1-9 (1981).
Wellman et al., "Magnetically-Assisted Transport Evanescent Field Fluoroimmunoassay," *Anal. Chem.* 78(13):4450-6 (2006).

(56) References Cited

OTHER PUBLICATIONS

Wilson et al., "Use of the IUL Countermat Automatic Colony Counter for Spiral Plated Total Viable Counts," *Appl. Environ. Microbiol.* 61:3158-3160 (1995).

Wolniak et al., 2004. BSCI 427 Principles of Microscopy Fall 2004 Syllabus, (http://www.life.umd.edu/cbmg/faculty/wolniak/wolniac/micro.html), printed Nov. 8, 2007, p. 1-8.

Yasui et al., "Imaging of *Lactobacillus brevis* Single Cells and Microcolonies Without a Microscope by an Ultrasensitive Chemiluminescent Enzyme Immunoassay with a Photon-Counting Television Camera," *Appl. Environ. Microbiol.* 63:4528-4533 (1997).

Zhao et al., "Competitive Immunoassay for Microliter Protein Samples with Magnetic Beads and Near-infrared Fluorescence Detection." *Anal. Chem.* 76(7):1871-1876 (2004).

International Search Report for PCT/US2006/37410, completed May 29, 2008, mailed Jun. 4, 2008.

International Preliminary Report on Patentability for PCT/US2006/037410, issued Mar. 24, 2009.

Written Opinion of the International Searching Authority for PCT/US2006/037410, completed May 29, 2008, mailed Jun. 4, 2008.

English translation of Japanese Patent Application No. H11-346795, filed Feb. 28, 1985.

English translation of Japanese Patent Application No. H3-83598, filed Aug. 29, 1989.

Kroll et al. "A laser-light pulse counting method for automatic and sensitive counting of bacteria stained with acridine orange," *Journal of Applied Bacteriology*, 66:161-167 (1989).

Moore et al, "Lymphocyte fractionation using immunomagnetic colloid and a dipole magnet flow cell sorter," *Journal of Biochemical and Biophysical Methods* 37:11-33 (1998).

Nelis and Van Poucke, "Enzymatic detection of coliforms and *Escherichia coli* within 4 hours" *Water Air and Soil Pollution*, 123:43-52 (2000).

Van Poucke and Nelis, "Solid phase cytometry-based enzymatic detection of coliforms in drinking water within 4 h", *Water Supply* 17:67-72 (1999).

Van Poucke and Nelis, "Rapid detection of fluorescent and chemiluminescent total coliforms and *Escherichia coli* on membrane filters" *Journal of Microbiological Methods*, 42:233-244 (2000).

Van Poucke and Nelis, "A 210-min solid phase cytometry test for the enumeration of *Escherichia coli* in drinking water," *Journal of Applied Microbiology*, 89:390-396 (2000).

Vidon et al. "A simple chemiluminescence-based method for rapid enumeration of *Listeri* spp. microcolonies," *Journal of Applied Microbiology*, 90:988-993 (2001).

Catalogue of Becton, Dickinson and Company, Japan, 2003.

Office Action (JP 2008-532493) with English translation, issued Jun. 16, 2011.

Extended European Search Report for EP 06804147.4, issued Jul. 4, 2011.

Findlay et al., "Automated closed-vessel system for in vitro diagnostics based on polymerase chain reaction," Clin Chem. 39(9):1927-33 (1993).

Freydiere et al., "Detection of salmonellae by using Rambach agar and by a C8 esterase spot test," J Clin Microbiol. 29(10):2357-9 (1991).

Gray et al., "Identification of micro-organisms after milliflex rapid detection—a possibility to identify nonsterile findings in the milliflex rapid sterility test," PDA J Pharm Sci Technol. 65(1):42-54 (2011).

Loats Associates Inc. System Specifications, "Ordering from Loats Associates, Inc.," <http://www.loats.com/order_info.html>, retrieved Apr. 12, 2005 (7 pages).

London et al., "An Automated System for Rapid Non-Destructive Enumeration of Growing Microbes," PLoS One 5(1):e8609 (16 pages) (2010).

Patterson, "A wide angle camera for photographic search of the ocean bottom," SPIE. C-XII-1-8 (1966).

Porter et al., "The use of DAPI for identifying and counting aquatic microflora," Limnol Oceanogr. 25(5):943-8 (1980).

Sage et al., "A rapid and nondestructive method for microbiological testing in pharmaceutical manufacturing." American Biotechnology Laboratory. 1-5 (2006).

\* cited by examiner

FIG. 1A

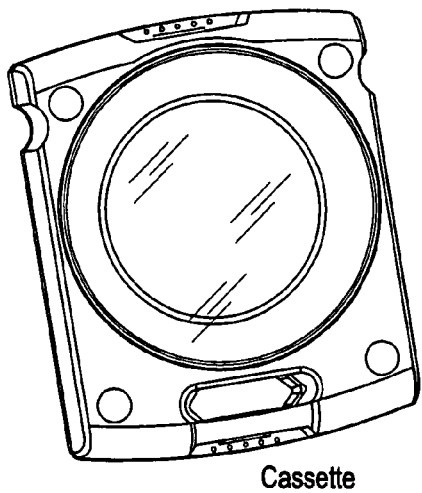

Cassette

FIG. 1B

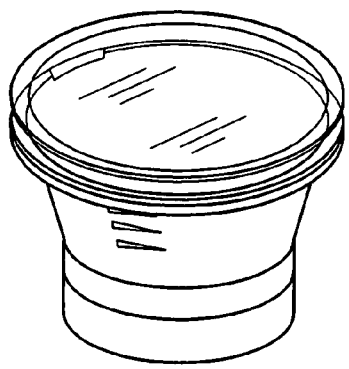

Funnel

FIG. 2

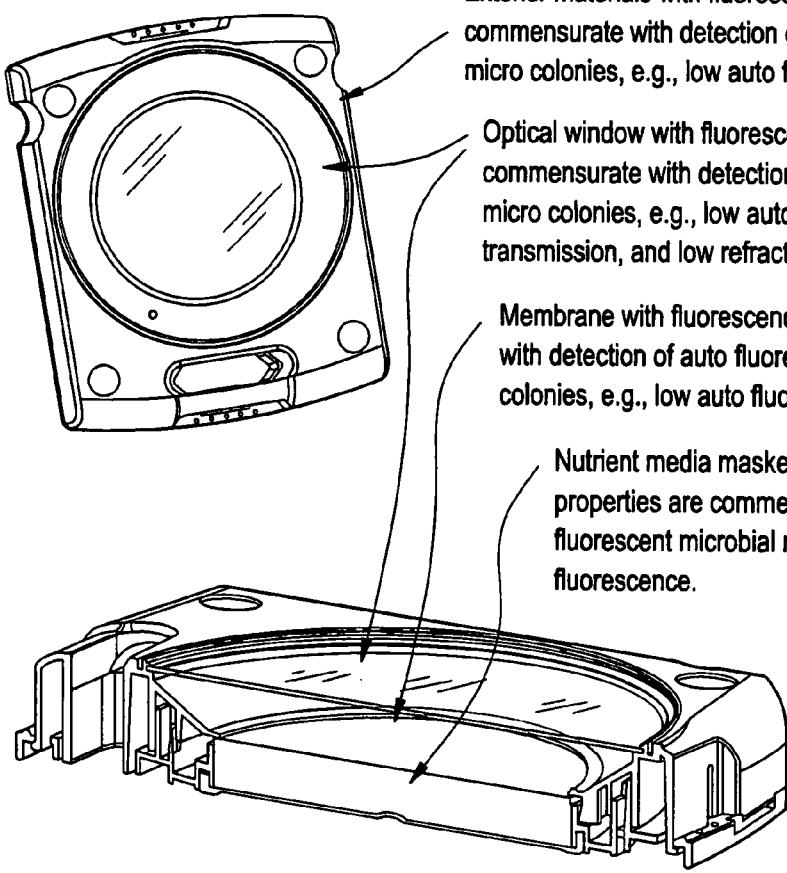

Exterior materials with fluorescence properties commensurate with detection of auto fluorescent microbial micro colonies, e.g., low auto fluorescence.

Optical window with fluorescence properties commensurate with detection of auto fluorescent microbial micro colonies, e.g., low auto fluorescence, high transmission, and low refraction.

Membrane with fluorescence properties commensurate with detection of auto fluorescent microbial micro colonies, e.g., low auto fluorescence.

Nutrient media masked such that fluorescence properties are commensurate with detection of auto fluorescent microbial micro colonies, e.g., low auto fluorescence.

Cutaway view

Growth Cassette
Elements of air management
and enhanced tortuous path

Sealable Walls form upper half of air management channel, Mate to lower channel

Air channel and inlets to media chamber

Cutaway 3x, air breather holes

Elements of side filled, fully entrapped media and method to create raised, proud media surface All surfaces of media secured and in contact with cassette at A, B, and C A) Media engages cassette bottom floor
B) Media engages circumferential wall
C) Media engages pouring lid underside FIG. 4B
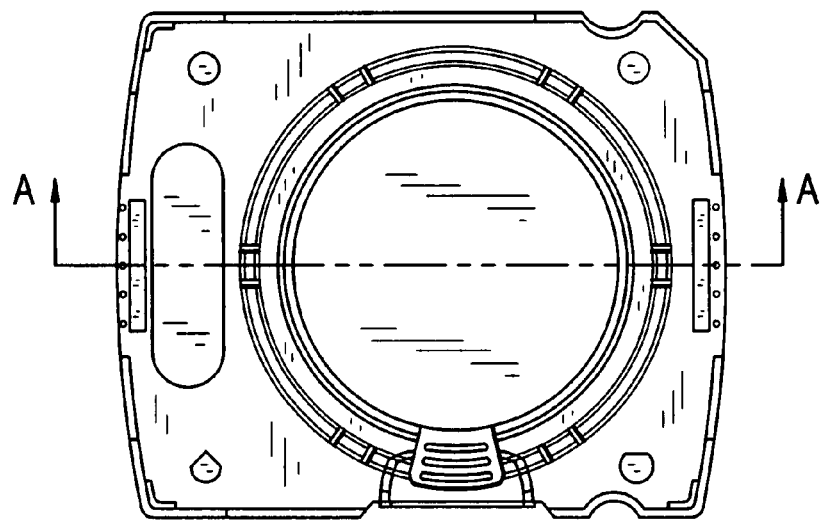
SECTION A-A
FIG. 4C
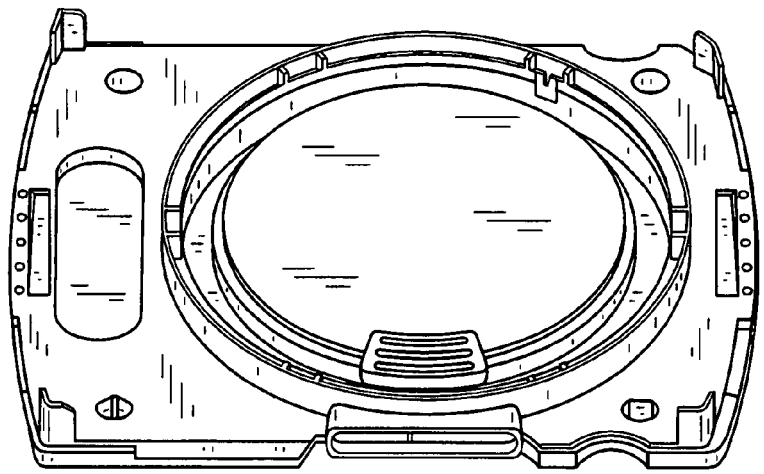
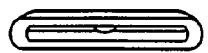

Fr ←         ↓Fd         → Fr
Underside     Surface A
Molded with concave surface, such that radial side loads "Fr" used to retain lid to the cassette produce force "Fd" pulling surface A to be flat.

Media is exposed forming raised and proud surface when pouring lid is removed

FIG. 9C
FIG. 9D
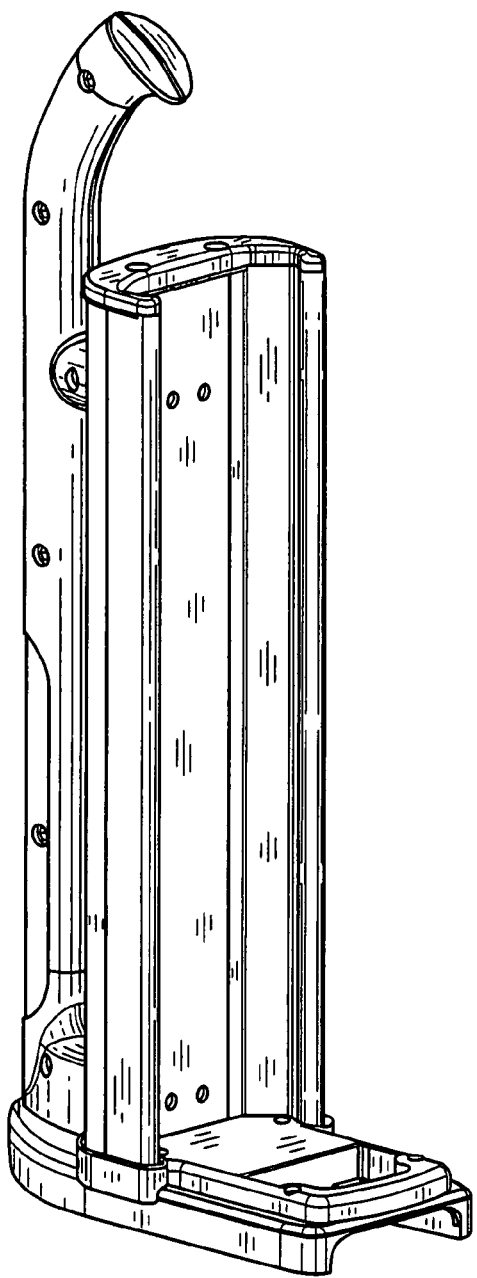
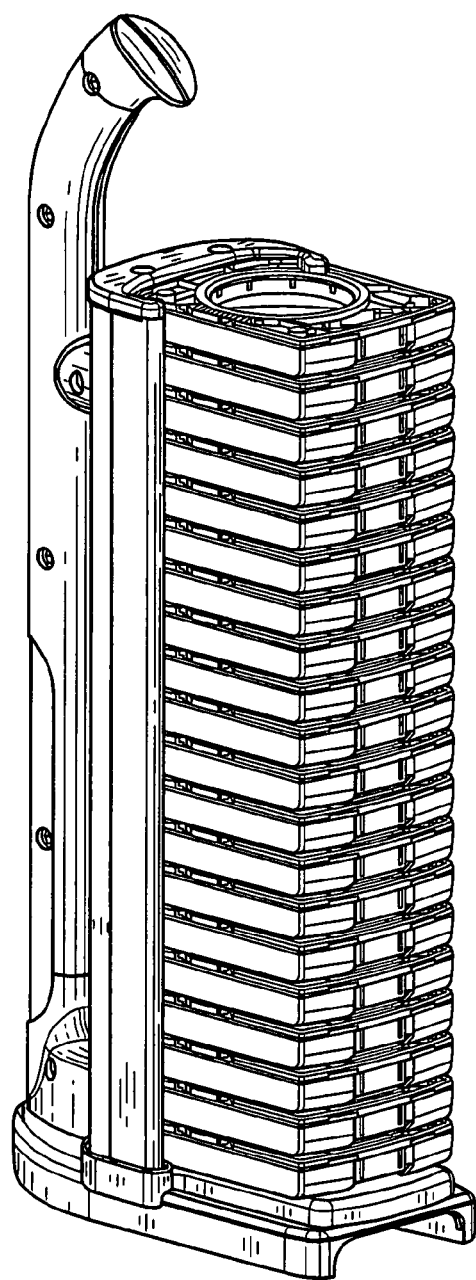

FIG. 10A
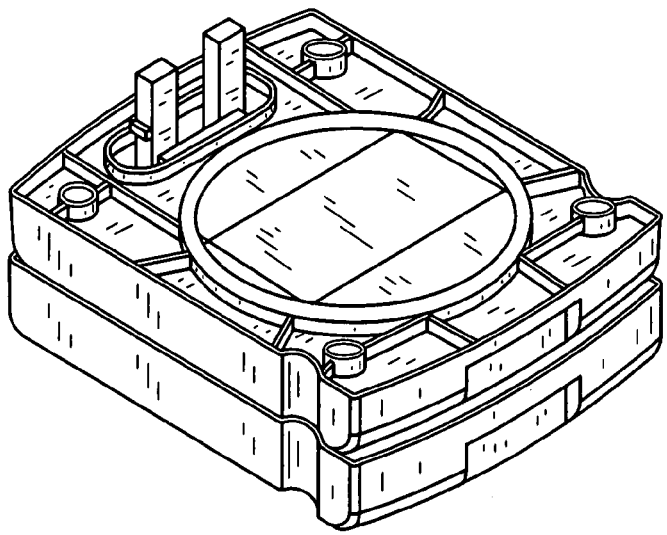
FIG. 10B
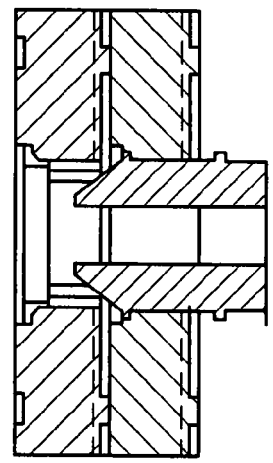
FIG. 10C
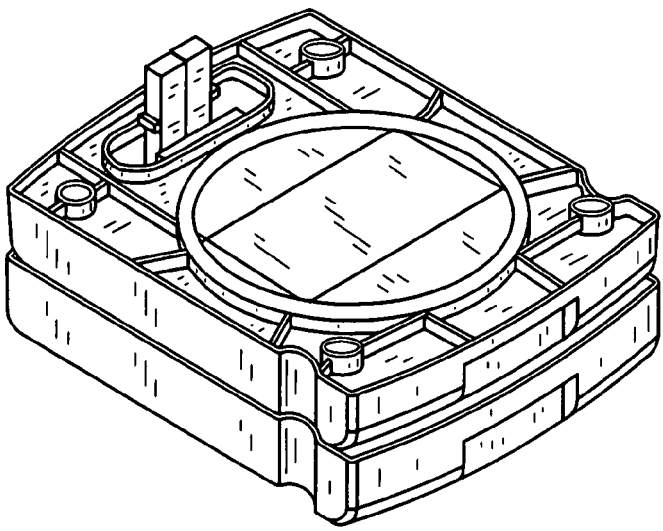
FIG. 10D
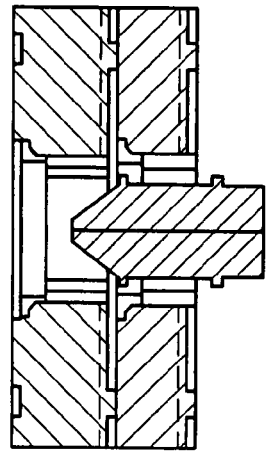
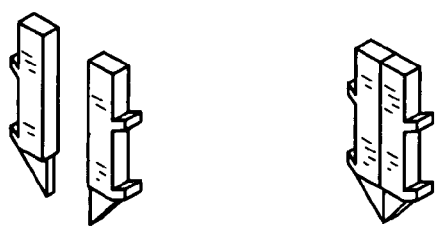

Through hole in mask, allows brighter plastic behind or brighter media to shine and fluoresce through Interface to standard lab-ware rubber stopper Interface to standard manifold pump heads

CASSETTE CONTAINING GROWTH MEDIUM

CROSS-REFERENCE TO RELATED APPLICATIONS

This application claims benefit of U.S. Provisional Patent Application No. 60/720,683, file Sep. 26, 2005, which is hereby incorporated by reference.

BACKGROUND OF THE INVENTION

The invention relates to the fields of cell culture and detection.

In many industries, particularly the food, beverage, healthcare, electronic, and pharmaceutical industries, it is essential to rapidly analyze samples for the degree of contamination by microorganisms, such as bacteria, yeasts, or molds.

One microbial culture technique, called microbial enumeration or colony counting, quantifies the number of microbial cells in a sample. The microbial enumeration method, which is based on in situ microbial replication, generally yields one visually detectable "colony" for each microbial cell in the sample. Thus, counting the visible colonies allows microbiologists to determine the number of microbial cells in a sample accurately. To perform microbial enumeration, bacterial cells can be dispersed on the surface of nutrient agar in Petri dishes ("agar plates") and incubated under conditions that permit in situ bacterial replication. Microbial enumeration is simple, ultra-sensitive, inexpensive, and quantitative but is also slow. The long time required results in increased costs in healthcare and in manufacturing. More rapid enumeration methods have been developed but, while shortening the time required, they have sacrificed one or more of the critical advantages of microbial culture.

There is a need for additional culturing devices and methods for microbial enumeration.

SUMMARY OF THE INVENTION

The invention provides a cell culture device—referred to as a cassette—that includes a housing that contains growth medium for microorganisms, wherein at least a portion of said housing is substantially non-radiative. The device may further include a detachable, sealable lid having an optically clear window disposed to allow imaging of the growth medium. This lid may be the substantially non-radiative portion of the housing. Preferably, the window and housing are substantially non-radiative, substantially non-reflective, or both. The housing may also include openings that provide for a tortuous passage of gases from the growth medium to the ambient environment, e.g., so that the housing has a gas exchange cross-sectional area of <15 mm². The device may further include a removable lid in conformal contact with the growth medium. Removing the lid exposes the growth medium, e.g., for contact with microorganisms.

The cassette of the invention may also be provided in a kit for detecting microorganisms together with a membrane adapted to be placed over the growth medium such that microorganisms deposited on the membrane receive nourishment from the medium. The kit may further include a filtration vessel that allows the membrane to collect microorganisms from a sample passed through the membrane. In one embodiment, prior to being placed over the medium, the membrane remains substantially planar during the passing of the sample through the membrane whereby microorganisms are deposited on the membrane. Preferably, the membrane is substantially non-radiative or black or both.

The cassettes and kits of the invention may be used in any method for growth, assay, or maintenance of microbes, including enumeration, detection, diagnosis, or therapeutic response.

By a "non-radiative" object is meant an object that does not emit light, e.g., by fluorescence, phosphorescence, or luminescence.

By a "non-reflective" object is meant an object that reflects less than 25%, 10%, 5%, 1%, or 0.1% of the light used to image the object.

Other features and advantages will be apparent from the following description and the claims.

BRIEF DESCRIPTION OF THE DRAWINGS

FIG. 1A is a schematic depiction of the imaged side of a cassette of the invention. FIG. 1B is a schematic depiction of a funnel that may be employed in conjunction with a cassette of the invention.

FIG. 2 is a schematic depiction of the imaged side of a cassette and a cross-section of the cassette. The elements of the cassette that allow for detection of auto-fluorescence from microbial colonies are indicated.

FIGS. 4B-4C are various schematic views of the cassette containing growth media.

FIGS. 10A-10D are schematic depictions of automated gripping and release of a cassette.

Figure 3A:
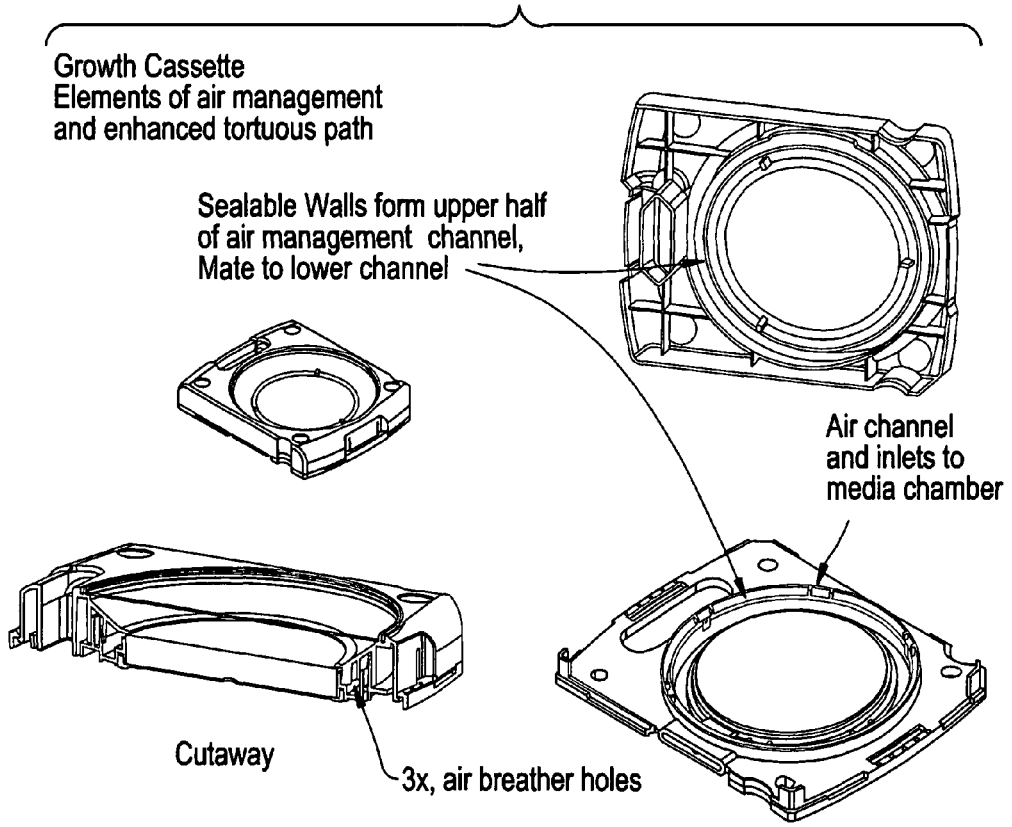
FIG. 3A is a schematic depiction of various views of a cassette showing the air management channels.

The figures are not necessarily to scale

DETAILED DESCRIPTION OF THE INVENTION

The invention features devices for capturing and culturing cells (e.g., microorganisms, cells containing microorganisms, or cells from eukaryotic cell cultures) and methods of using these devices. One device is a cassette containing growth media (also referred to as nutrient media) that may be employed in an automated rapid enumeration system such as the Growth Direct™ system, e.g., as described in U.S. Publication No. 2003/0082516, which is hereby incorporated by reference. Another device is a filtration funnel that may used to concentrate cells in a sample onto a membrane. An exemplary cassette and a filtration funnel assembly are shown in FIGS. 1A-1B.

The Growth Cassette™ is an advanced device that has, for example, been enhanced with features for controlling surface flatness, optical imaging, controlled dehydration of semi solid nutrient media, controlled air and particle exchange, and automated handling. These attributes enable, e.g., automated imaging of microbial growth. Any solid or semi-solid growth media can be employed in the present cassette. Examples include Sabouraud dextrose agar (SDA), R2A agar, tryptic soy agar (TSA), and plate count agar (PCA).

In various embodiments, the cassette facilitates automated imaging of autofluorescent microbial microcolonies containing fewer than 500 cells, for example, by employing materials with fluorescence properties commensurate with such detection. An exemplary material is black K-Resin® (styrene-butadiene-copolymer; Chevron Phillips). The cassette may also employ a transparent lid that has fluorescence properties commensurate with detection of autofluorescent microbial microcolonies. An exemplary material for the lid is Zeonor® 1060R (polycycloolefin resin; Zeon Chemicals LP). Glass may also be employed. A porous membrane may also be employed that has fluorescence properties commensurate with detection of autofluorescent microbial microcolonies. Membranes may be manufactured from materials including cellulose, cellulose acetate, polystyrene, polyethylene, polycarbonate, polyethylene terephthalate, polyolefin, ethylene vinyl acetate, polypropylene, polysulfone, polytetrafluoroethylene, nylon, and silicone copolymer. The choice of membrane depends, in part, on the type of cell to be cultured (e.g., microorganisms that grow attached to a surface (anchorage-dependent), microorganisms that grow in suspension (anchorage-independent), or microorganisms that grow as attached to a surface or in suspension), degree of permeability, and rate of transfer of fluids and gases. An exemplary membrane is a black mixed cellulose ester membrane (Sartorius AG). Portions of the cassette that will not be imaged may be made of any suitable material, e.g., acrylonitrile-butadiene-styrene or styrene-acrylonitrile.

Preferably, a cassette has minimal air exchange with the ambient environment (e.g., air exchange cross sectional area of <15 mm$^2$, or less than half that of a Petri dish of comparable area) to minimize media dehydration. The air management system may also include enhanced tortuous air paths to eliminate microbial incursion into the cassette interior.

The cassette may also be designed for introducing nutrient media through a face other than the face that is proximal and parallel to the growth surface, i.e., from the side. Such a cassette may include a port on the edge of the cassette. The media in a cassette may also be sealed prior to use to minimize dehydration. Such cassettes have media encapsulated on the top, bottom, and sides. A flat media surface desirable for planar imaging may be achieved through the design of a removable pouring lid and method for pouring lid retention post sterilization, e.g., by including glass beads to prevent relaxation of the plastic and detachment from nutrient medium. Preferably, the media is proud with respect to the material of the cassette. This configuration allows for the retention of flatness as the media dries during use. Typically, media is highly fluorescent, and the invention allows for the use of a porous membrane to cover the media to reduce background emission. The cassette may also feature a mask, i.e., a rim, that covers the edges of the membrane, and any exposed media, during use.

Preferably, a cassette is capable of being stacked in a carrier, e.g., designed to transfer and introduce a group of cassettes to an automated imaging instrument. Such automated handling of a cassette may include transport, interfacing between the cassette and carrier, positioning for automated handling, and capability for robotic transfer. The cassette may also be designed to allow for reproducible mechanical positioning, i.e., repeatedly being able to return the same cassette to same location for automated imaging.

A cassette may also include design features that facilitate alignment of multiple images. Imaging fiducial marks include a through hole aperture over fluorescent plastic or media. Imaging fiducial marks also include printed or embossed fluorescent material on cassette. Other fiducial marks are known in the art.

The funnel of the invention may be employed to capture on a membrane, e.g., by size-based filtration, microorganisms present in a sample, which may be liquid or air. Capture is achieved by introducing the medium, e.g., a liquid or gas sample, to be filtered in the funnel and creating a pressure difference to cause the medium to flow through the membrane. The membrane may then be contacted with a growth medium in a cassette, e.g., by manual transfer from the funnel assembly. Microorganisms on the membrane may then grow into colonies and be imaged, e.g., according to the methods of U.S. Publication No. 2003/0082516. Other methods for transferring the membrane or otherwise placing samples on the cassette are known in the art. Preferably, the filter includes a flat surface, e.g., sintered plastic beads from Porex, to support the membrane during filtration to reduce or prevent marks on the membrane. Concomitant with this feature, the filter may include access areas to allow for manipulation of the membrane without damage to the imaged area. The filter may also prevent media from passing through the edge of the membrane, e.g., to prevent microorganisms from depositing on the edges of the membrane that may be covered by the mask described above.

Cassettes with or without funnels may be employed in any method where microbial growth is desired, including detection, enumeration, diagnosis, and therapeutic response. Exemplary fields of use include testing liquid, air, or surface samples for microbial bioburden; testing industrial samples, sterile pharmaceutical product samples, non-sterile pharmaceutical product samples for microbial bioburden; and testing samples for anaerobic microbial bioburden. The cassettes are compatible with imaging autofluorescent microcolonies under anaerobic conditions and may include components for actively removing molecular oxygen (e.g., a gas-pack or equivalent). Any microbe, including bacteria, cyanobacteria, protozoa, fungi, mammalian cells, plant cells, or other eukaryotic cell, may be employed in conjunction with the cassette and funnel described herein.

The invention will now be further described with respect to certain preferred embodiments.

Cassette Facilities Auto Imaging of Autofluorescent Microbial Microcolonies

FIG. 2 shows elements of cassette materials that allow auto imaging of autofluorescent microbial microcolonies, e.g., that facilitates auto imaging of autofluorescent microbial microcolonies containing fewer than 500 cells. As is shown in the figure, the top surface is manufactured from (or coated with) a material that has low autofluorescence and reflection. The cassette includes an optical window to allow for imaging of microbes on a membrane disposed to cover growth media. The membrane is also not fluorescent.

Nutrient Media Controlled Drying Profile, Air Management

Figure 3B:
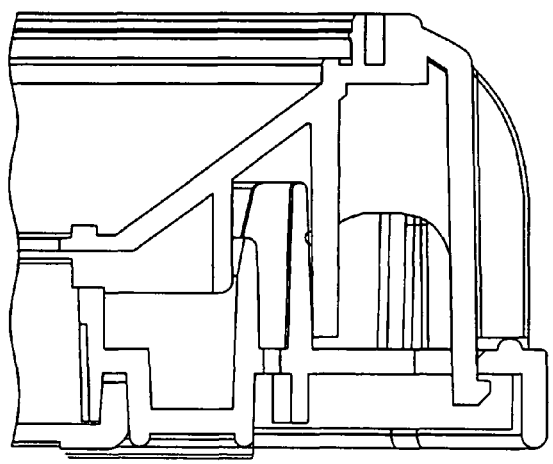
FIGS. 3B-3C are cross-sectional views of the cassette showing an inlet for air.
Figure 3C:
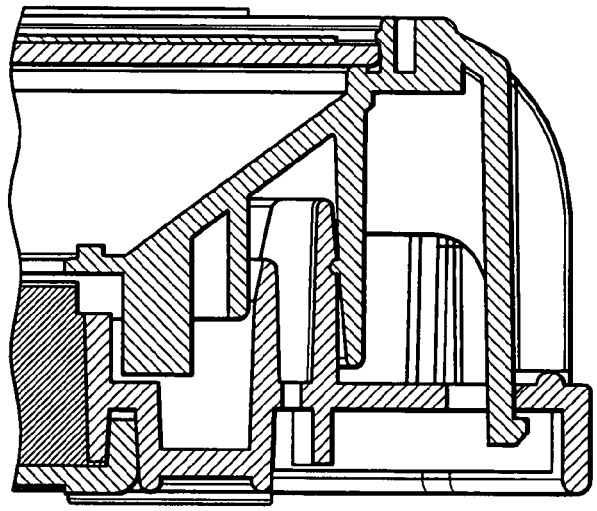

To achieve a flat nutrient media surface for imaging over multiple days, we have invented a minimum air exchange passage system, whereby the microorganisms are delivered sufficient oxygen for growth promotion, but the air exchange is greatly limited compared to a standard Petri dish. The flow of the air and its impingement upon the media surface is managed to provide uniform drying of the nutrient media. FIGS. 3A-3C show elements of the air management system. FIG. 3A illustrates how two halves of a cassette may be mated to produce a tortuous air path. FIGS. 3B-3C show a close-up view of an air hole and its spatial relation to the media.

Figure 4A:
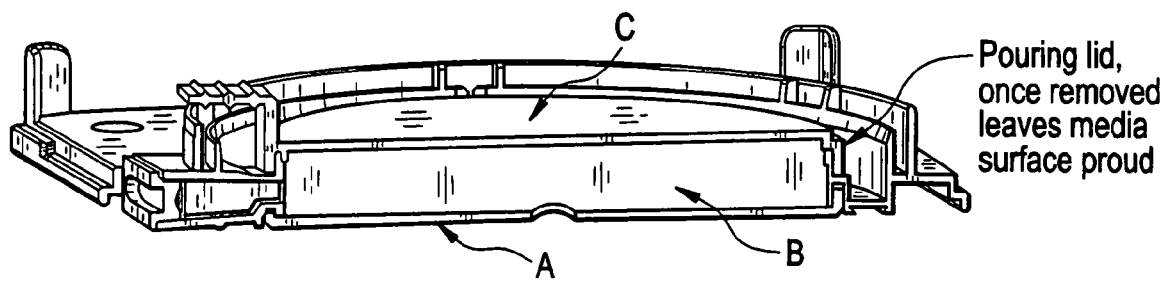
FIG. 4A is a schematic depiction of growth medium disposed in a cassette.

Sealable Nutrient Media Cassette, Fillable Via a Port on the Edge of the Cassette To retain and encapsulate the nutrient media within the cassette so that it is contacted with the circumferential side walls and the back or bottom surface as well as a third surface formed by the removable pouring lid, we have invented a side fill cassette that is fully sealed post filling. The side filled cassette allows the media to be encapsulated over 100% of its surface area (top, bottom, and sides). The sealed cassette provides for greater shelf life and prevents media drying while in storage. To prevent trapped air bubbles from accumulating in the media, we may utilize a split overfill chamber. FIGS. 4A-4C show elements of the side filled, sealable cassette.

Flat Media Surface for Imaging, Achieved Thru Design of Removable Pouring Lid and Design Method for Pouring Lid Retention Post Sterilization.

To achieve a flat media surface for imaging, we have designed a removable pouring lid with a radial lip to seal to the cassette. The profile of the lid's underside surface may be flat or contoured such that the radial retention loads counteract and create a flat surface. A specially designed top surface, gate, and process controls allow the material to be fed into the mold to prevent any disturbance or visible blush to the underside of the lid, i.e., the surface of the lid is smooth. Glass beads may be embedded into the resin to counteract the creep effects of plastic under load and the creep effects induced through common sterilization methods, such as gamma irradiation. The combined effect of these attributes is a pouring lid that allows for rapid impingement of the molten liquid media during filling without being displaced or bowing or warping.

Figure 5A:
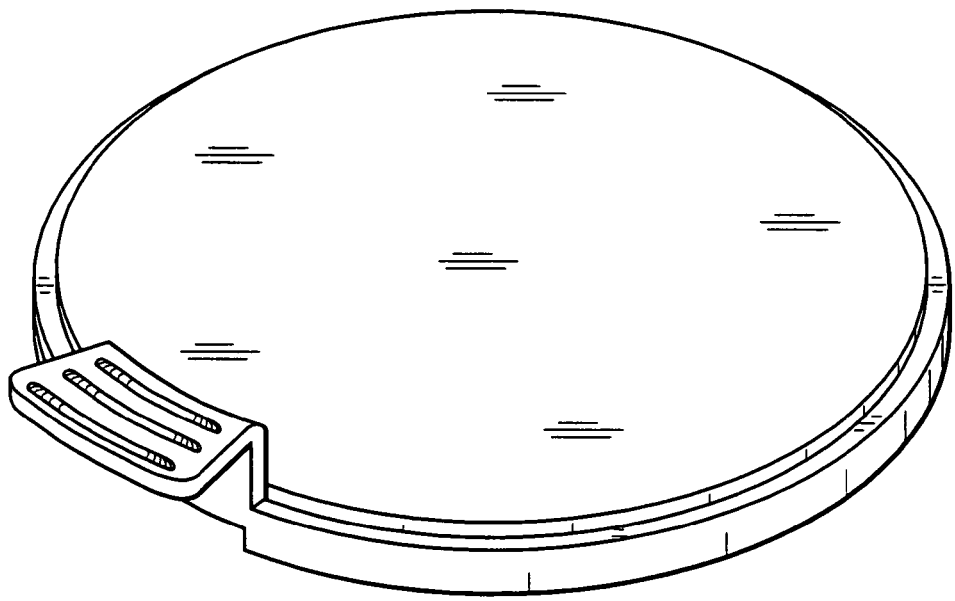
FIG. 5A is a schematic depiction of a removable lid against which growth media is cast.
Figure 5B:
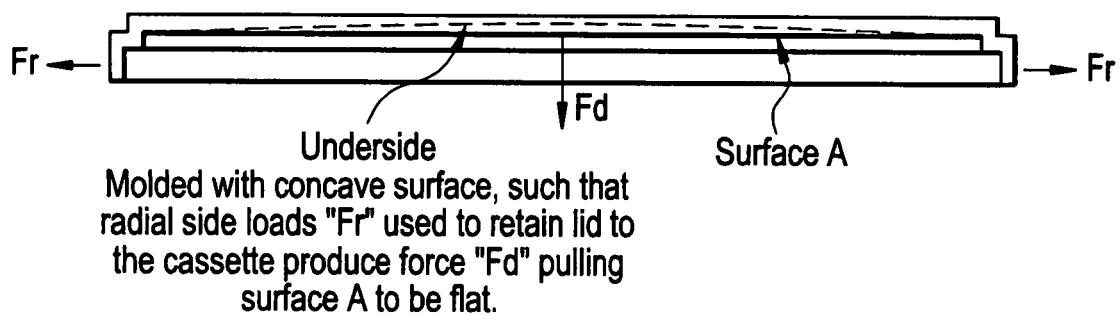
FIG. 5B is a schematic depiction of the forces acting on the growth media.

FIGS. 5A-5B show elements of the flat media surface for imaging, achieved thru design of removable pouring lid and design method for pouring lid retention post sterilization.

Design Method of Maintaining Flat Media Surface for Imaging Over Multiple Days by Means of Proud Nutrient Media To allow the media the opportunity to shrink as it dries in a controlled flat manner, we have designed a feature to have a portion of the media proud compared to the cassette side walls. This feature prevents any interaction and restriction to the edge of the media that would occur if it were in contact and subject to resistance of movement.

Figure 6:
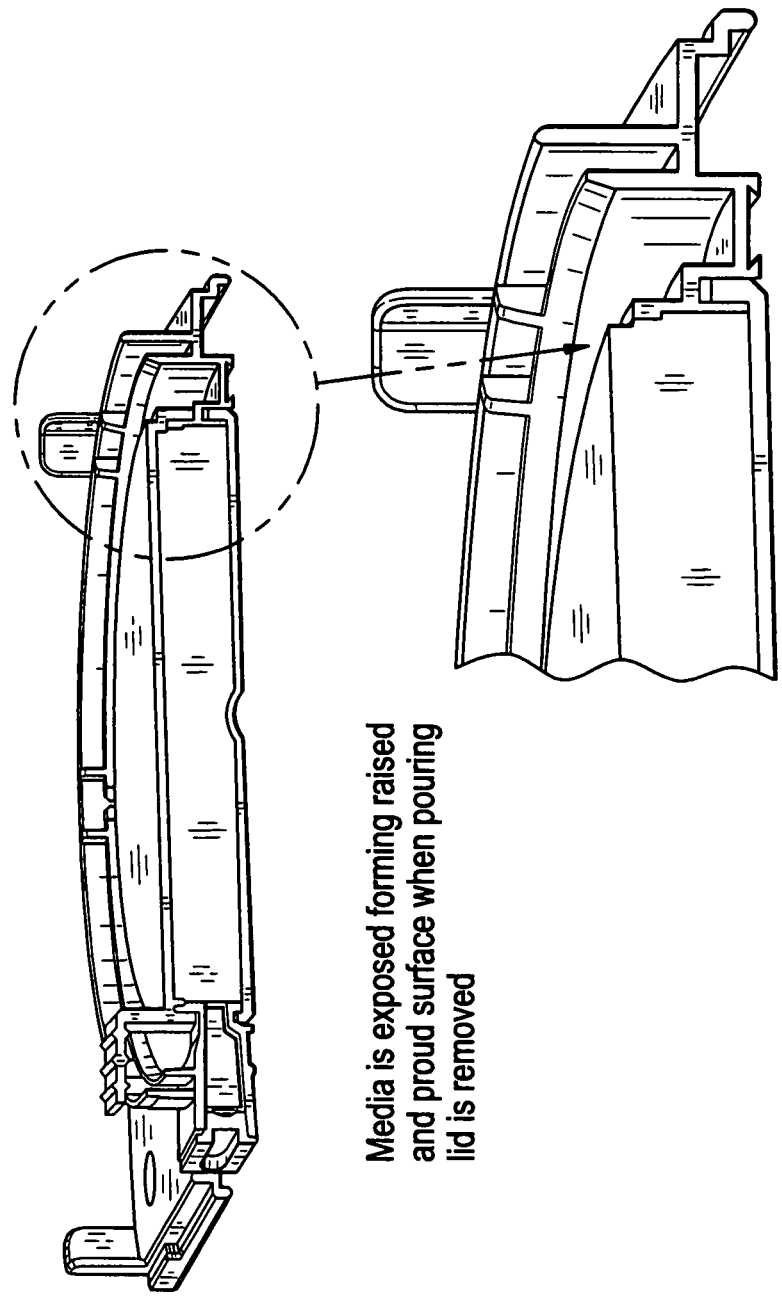
FIG. 6 is a schematic depiction of the removal of the lid from the cassette yielding raised and proud growth media surface.

FIG. 6 shows elements of the design method of maintaining flat media surface for imaging over multiple days by means of proud nutrient media.

Design to Block Fluorescence from the Nutrient Media

The cassette specifically uses a low fluorescent, e.g., flat black, membrane to cover the highly fluorescent nutrient media agar. To cover the edge effects where the membrane, e.g., mixed cellulose ester, may not completely cover the media or where absorption and drying create a bright fluorescent edge to the membrane, we have designed a mask to cover this region. To prevent the mask from reflecting light back to the imager, the mold surfaces of the mask are treated to form a vapor honed non reflective surface. The mask may be an integral component of the cassette lid.

To prevent microorganisms from being deposited in this masked zone, we may seal the membrane during filtration, such that the growth area formed is kept within the imaged area over the duration of the test as the media receeds. This design approach of controlled growth zone and controlled masking zone may also be used to negate user membrane placement error.

Figure 7:
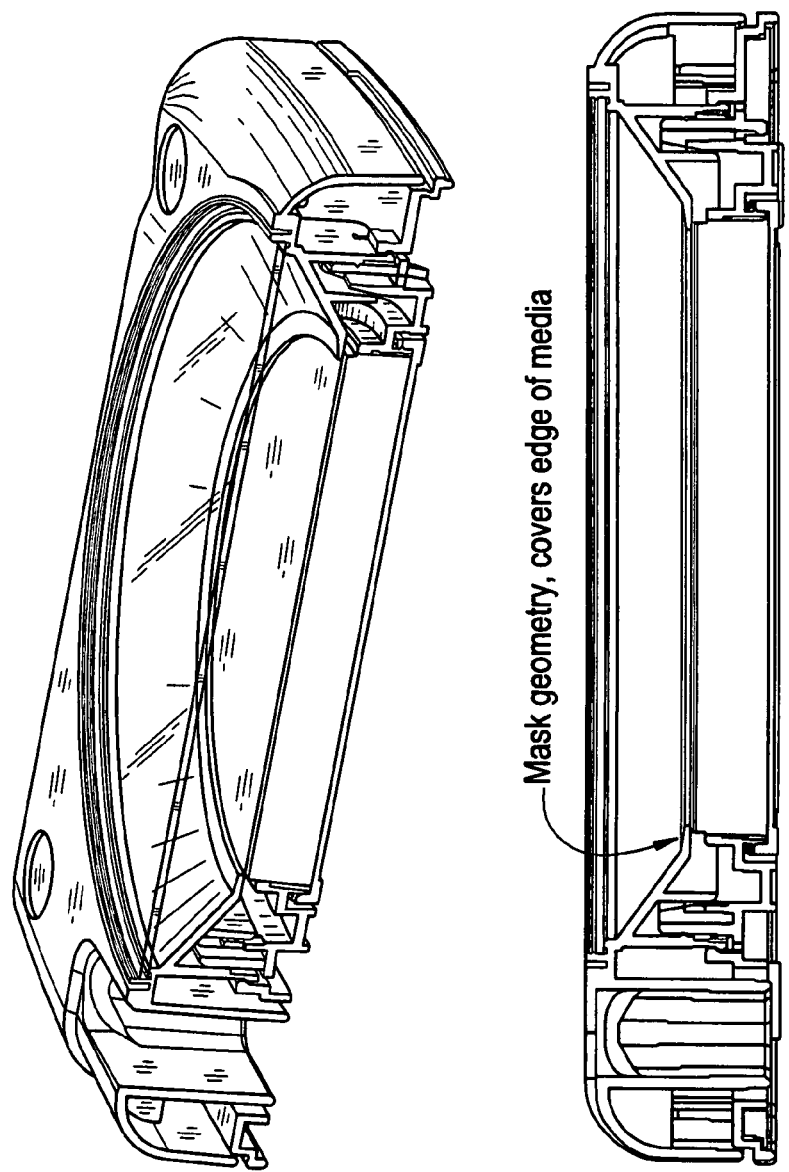
FIG. 7 is a schematic depiction of the cross-sectional views of a cassette illustrating a masking feature that covers the edges of a membrane disposed on top of growth media.

FIG. 7 shows elements of the mask to block fluorescence from the nutrient media.

Enhanced Tortuous Air Path

Traditional Petri dishes and Rodac plates provide for a controlled growth environment by means of a tortuous air passage. We have enhanced this significantly to allow for rapid movement and flipping associated with automatic robotic handling and plate processing. We have designed multiple convolutions and entrapment zones in the cassette's tortuous air management system. FIGS. 3A-3C show elements of the enhanced tortuous air path.

Method to Retain and Seal Optical Window

Figure 8:
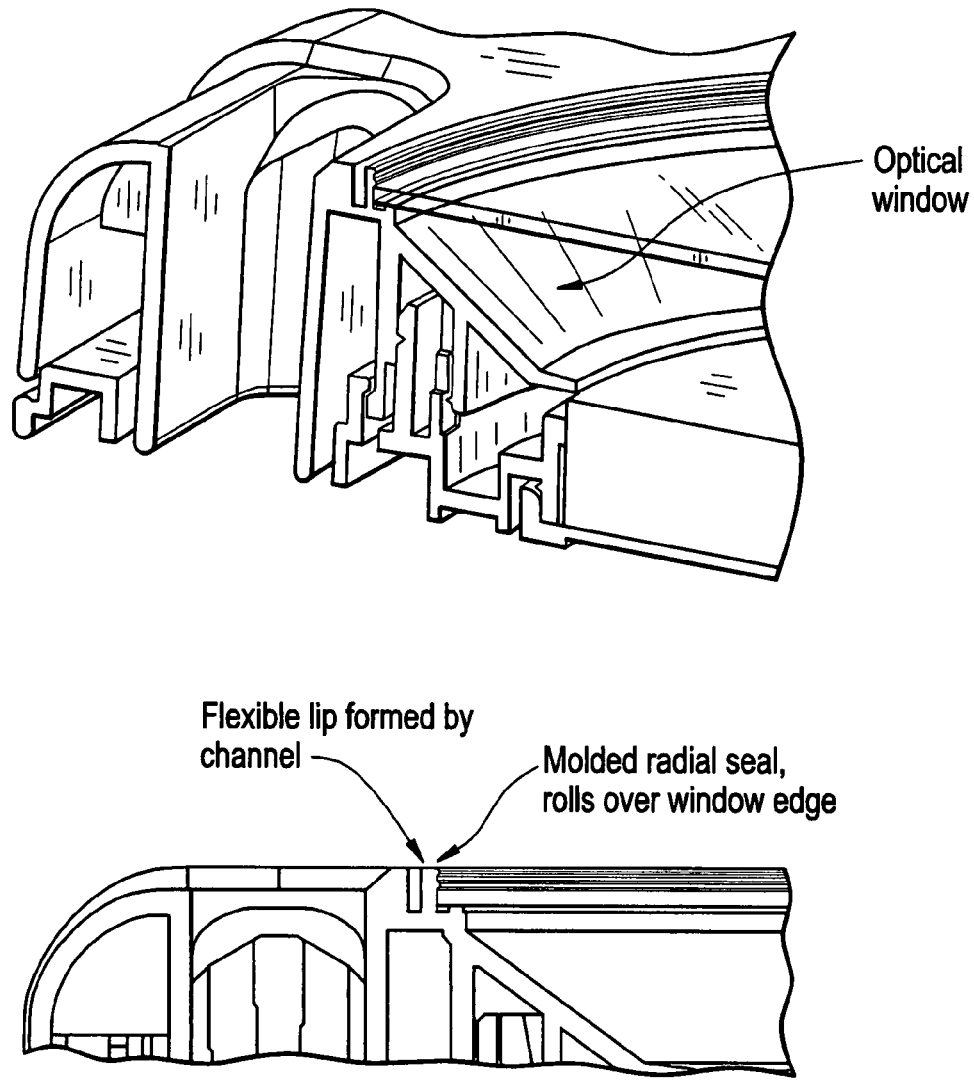
FIG. 8 is a schematic depiction of the sealing of an optical window to the cassette.
Figure 9B:
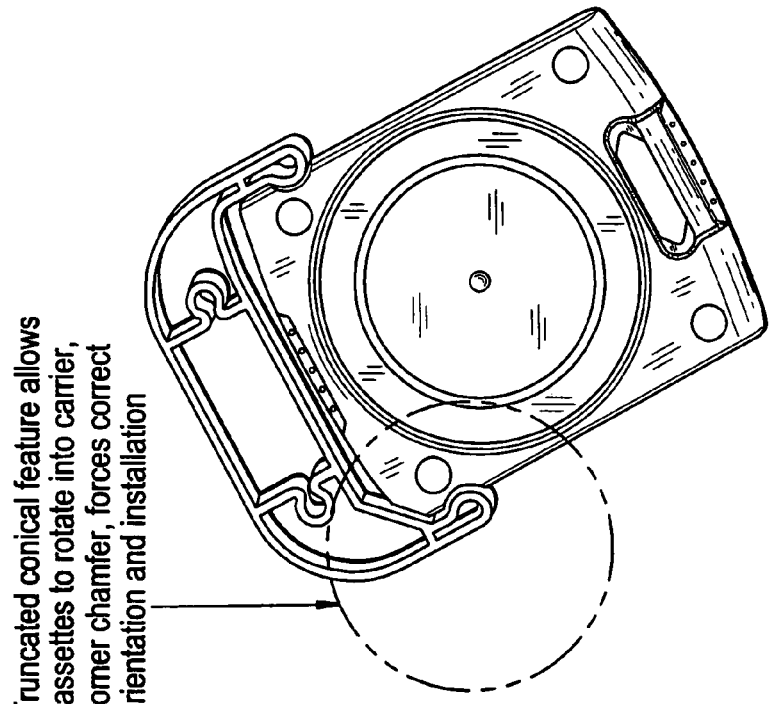
FIGS. 9A-9B are schematic depictions illustrating how design elements of the cassette can be used to aid automatic loading of the cassette.
Figure 9A:
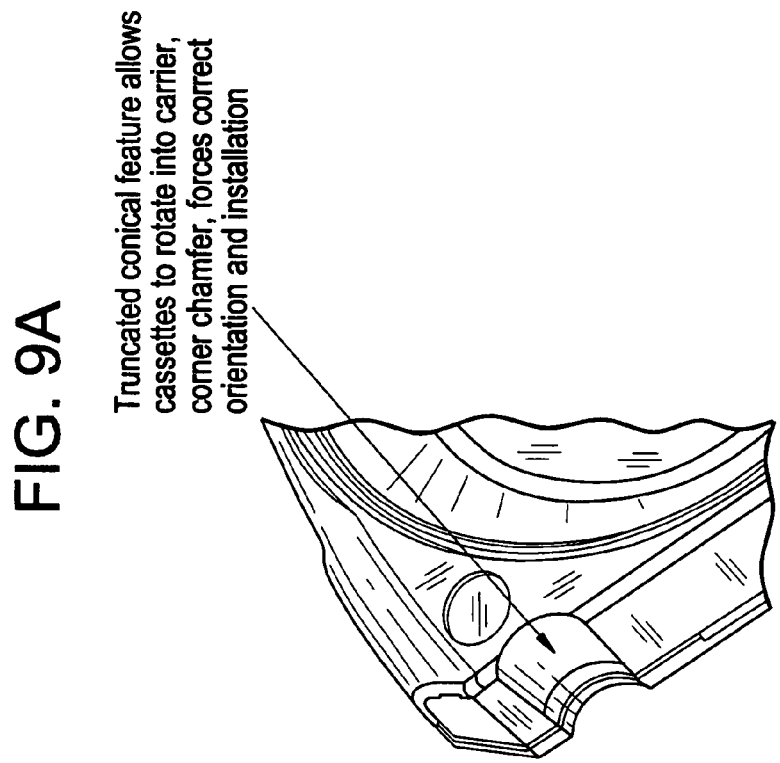
Figure 9E:
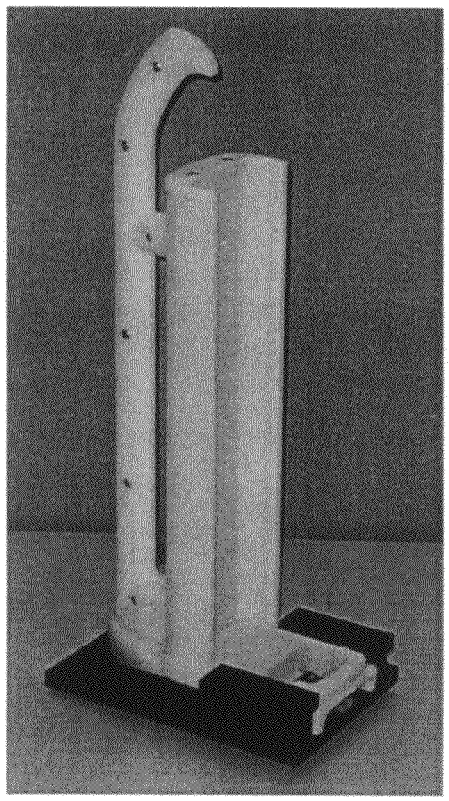
FIGS. 9C-9D are schematic depictions of a cassette carrier and a plurality of cassettes loaded in the carrier that allow for automatic manipulation of multiple cassettes.
Figure 9F:
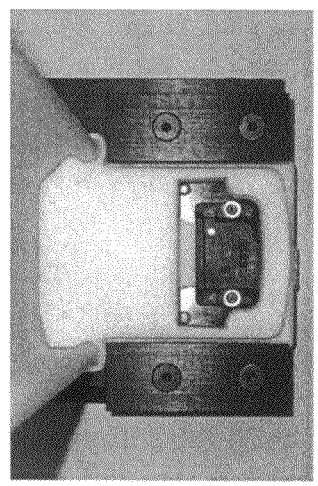
Figure 9G:
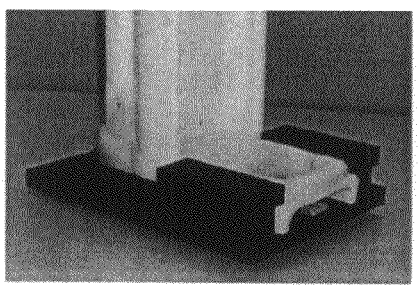
Figure 9H:
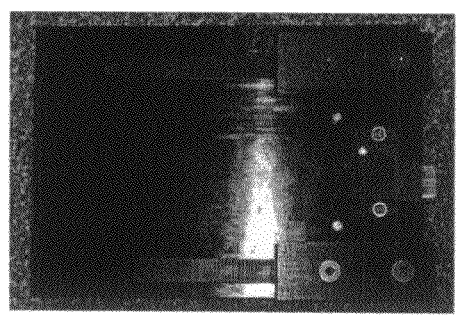

To retain and seal the optical window, e.g., fabricated in glass or plastic, we have designed an integral circumferential seal. Flexure of the retention element is achieved by deflecting into an open channel. This open channel design also allows the single piece molded design to be extracted from the mold tool. FIG. 8 shows elements of the design method to retain and seal optical window.

Cassette Transport Design, Carrier Interface, and Positioning for Automated Handling.

A desirable characteristic of the cassette is that it be capable of being repeatedly placed in the Growth Direct™ system, or other automatic imaging system. Also a carrier is desirably provided to transport cassettes from sample site to the imager. To achieve this result, we have designed a unique interface between the cassette and a cassette carrier—two half moon truncated cones. One truncated cone on each side of the cassette serves to key the cassette to the carrier device. A cassette may be rotated into position or deposited from the top. A large chamfer surface negates the miss installation of the cassette. The mating rod like features on the carrier engage the half moon feature, preventing a cassette from falling out in normal use. These features in conjunction with the carrier ensure the cassette is always properly placed for automatic robotic processing.

FIGS. 9A-9D show elements of the cassette transport design and cassette-carrier interface.

Method to Align Cassette to Axis of Automatic Processing Machine, Growth Direct.™

Automated cassette or plate handling may require that the system zero out or minimize cassette placement error relative to the robotic grip, or the system must know where the cassette is in space. We have designed a zero draft tapered wedge slot interface to the robotic system. Two blade like features on the automated robotic grip need only find any entry point into the slot, one in the act of expanding the grip outward cams the cassette to the line of action of the gripper and squares up the cassette.

FIGS. 10A-10D show elements of the method to align a cassette to an axis.

Imaging Fiducial Through Hole Aperture Over Fluorescent Plastic

Our system may employ the ability to know where the same cassette is placed relative to the imager, every time that same cassette is cycled through for imaging. To achieve this result, a through hole in the mask may be utilized to create a stepped, fluorescent mark in an image by having the upper most plastic, i.e., mask with through hole, be of lower natural fluorescence than the plastic structure behind, in this case the cassette base. With the brighter plastic behind, it illuminates the through hole creating a reproducible fiducial for accurate image placement.

An alternate means of providing the back fluorescence is to have the fiducial hole located over the nutrient media as the media inherently has a high degree of fluorescence.

Figure 11:
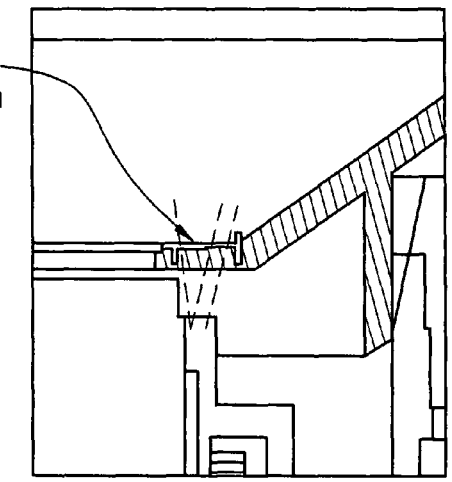
FIG. 11 is a schematic depiction of a through hole in the mask in the cassette that provides a fluorescent fiducial mark.

FIG. 11 shows elements of the imaging fiducial mark through hole aperture over fluorescent plastic.

Filtration Assembly Internal Seal Design and Use of Sintered Porous Plastic

Figure 12:
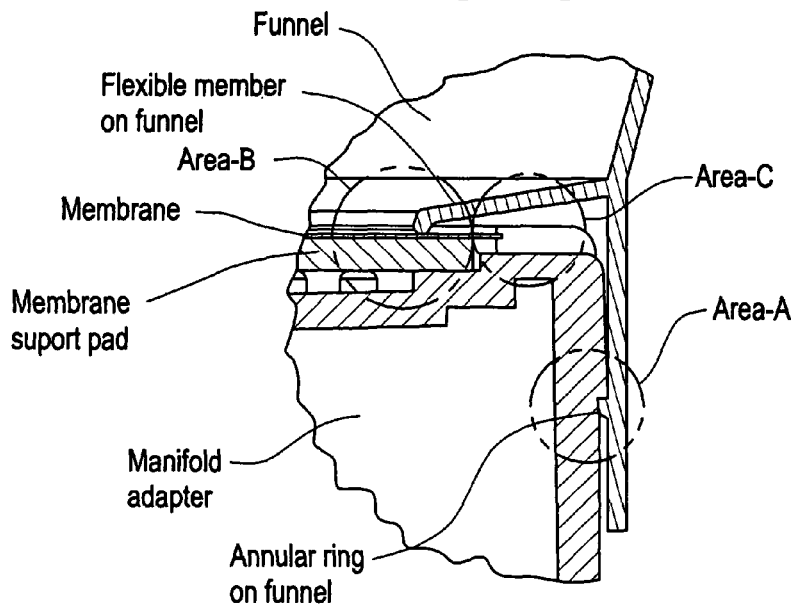
FIG. 12 is a schematic depiction of a funnel.

Any seal or noncontiguous stepped feature which contacts a membrane inherently leaves a mark on the membrane when it is released or removed. Many commercial funnel assemblies seal the membrane directly between two rigid plastic elements, leaving a circular ring indentation at that point. To prevent such a mark or indentation from appearing within our image zone, (image zone defined as the wetted area of the membrane on which microorganisms will grow), we have solved the problem as shown in FIG. 12. An inner seal traps the membrane to a porous plastic pad, e.g., made from sintered plastic beads, such as those available from Porex. The porous pad has specific properties and a smooth surface to prevent marring, wrinkling, or other perturbations to the membrane, which may interfere with imaging. Vacuum induces movement of air and liquid containing the organisms to pass through this porous barrier, leaving the microorganisms trapped on the membrane surface. An outer seal ensures vacuum is generated and flow occurs in the desired area.

FIG. 12 shows elements of the internal seal design and use of sintered porous plastic.

Filtration Assembly, Dual Mode Manifold Interface in a Single Device.

The filtration assembly may contain a molded plastic base referred to as the manifold adapter, unlike current products which are designed for a specific device. For example, either they fit a traditional rubber stopper (used in common bio safety cabinet manifold system) or they fit a common pump head system such as that produced by Millipore. The filtration assembly shown below has a dual interface. The center nozzle spout fits common stoppers and the lid of the base manifold adapter conforms to most pump head (tulip) assemblies.

Figure 13:
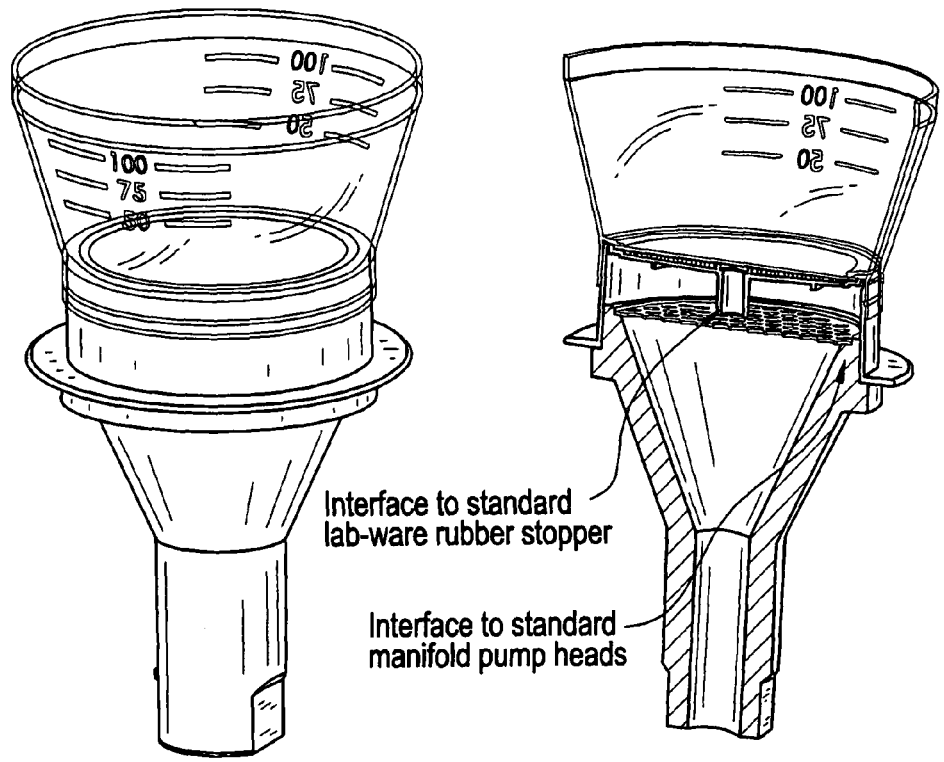
FIG. 13 shows various views of a funnel.

FIG. 13 shows elements of the dual mode manifold interface.

Filtration Assembly, Ease of Manual Membrane Removal by Means of an Integral Pocket for Grasping Edge of Membrane.

A common problem with current membrane filtration assemblies is the difficultly of grasping the membrane for manual transfer to the media. We have solved this problem through the use of integral pockets and raised castle protrusions that position the edge of the membrane for easy grasping with tweezers or forceps. This feature allows desirable membrane imaging as it works to keep the grip indentation from manual transfer out of the imaging zone.

Figure 14A:
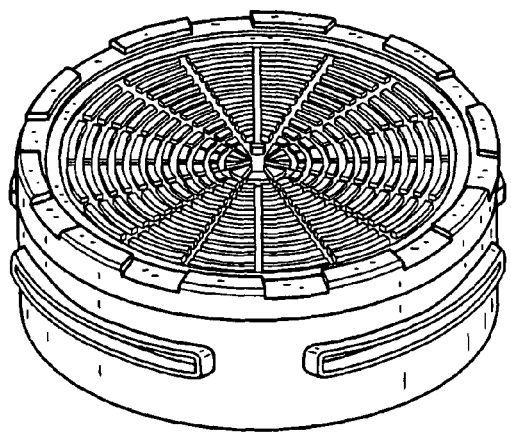
FIG. 14A is a schematic depiction of a manifold adaptor for use with a funnel.
Figure 14B:
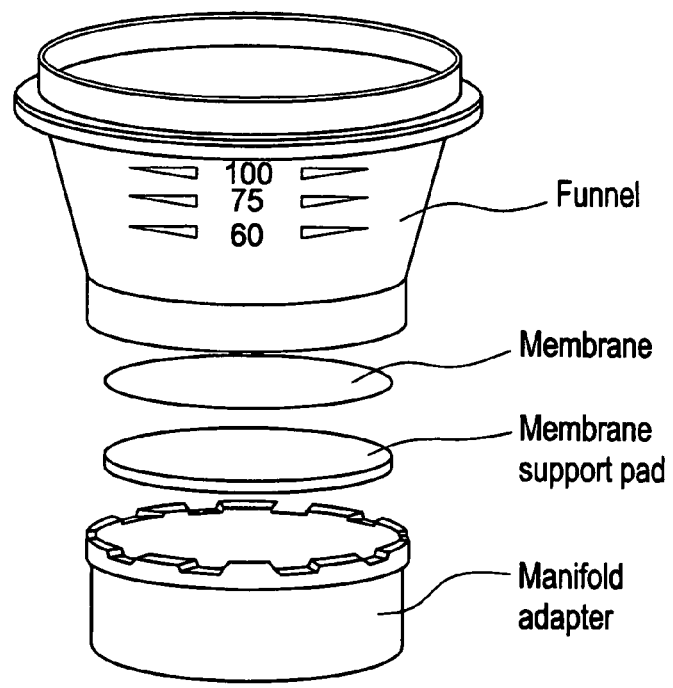
FIG. 14B is an exploded view of the components of a funnel.
Figure 14C:
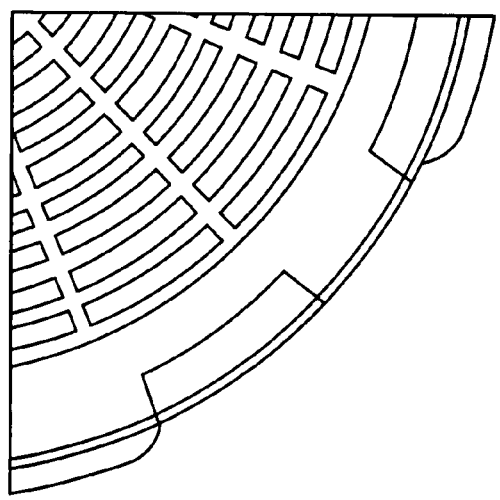
FIG. 14C is a schematic view of a component of a funnel having indentations for removing a membrane.

FIGS. 14A-14C shows elements of the integral pocket that allows forceps to access the edge of the membrane for ease of retrieval.

Other Embodiments

All publications, patents, and patent applications mentioned in the above specification are hereby incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:

1. A cell culturing device comprising a housing that contains growth medium for microorganisms; a detachable, sealable lid comprising an optically clear window disposed to allow imaging of said growth medium; a substantially non-radiative, substantially non-reflective rim that covers the edge of said growth medium; and a fiducial mark comprising a radiative component, wherein said device is configured to allow placement of a membrane over said growth medium so that said rim covers the edge of said membrane and any exposed growth medium.

2. The device of claim 1, wherein said window is substantially non-radiative.

3. The device of claim 1, wherein said window is substantially non-reflective.

4. The device of claim 3, wherein said housing and window are both substantially non-radiative and non-reflective.

5. The device of claim 1, wherein said housing includes openings that provide for a tortuous passage of gases from said growth medium to the ambient environment.

6. The device of claim 1, further comprising a removable lid in conformal contact with said growth medium.

7. The device of claim 1, wherein said growth medium is proud.

8. The device of claim 1, wherein said growth medium retains flatness as it dries.

9. The device of claim 1, wherein said radiative component comprises radiative plastic or growth medium.

10. The device of claim 9, wherein said radiative plastic or growth medium is imaged via a through hole in said rim.

11. The device of claim 1, wherein said radiative component comprises printed or embossed fluorescent material.

12. The device of claim 1, further comprising said membrane placed over the growth medium such that microorganisms deposited on the membrane receive nourishment from said medium.

13. The device of claim 1, wherein said radiative component comprises radiative growth medium.

14. A kit for detecting microorganisms, comprising the device of claim 1, together with a filtration vessel comprising a membrane that collects microorganisms from a sample passed through the membrane.

15. The kit of claim 14, wherein said membrane is adapted to be placed over the growth medium of the device of claim 1 such that microorganisms present in the sample and deposited on the membrane receive nourishment from said medium.

16. The kit of claim 14, wherein, prior to being placed over the medium, the membrane remains substantially planar during the passing of the sample through the membrane whereby microorganisms are deposited on the membrane.

17. The kit of claim 16, wherein the filtration vessel further comprises a porous pad having a smooth surface causing the membrane to remain substantially planar during the passing of the sample through the membrane whereby microorganisms are deposited on the membrane.

18. The kit of claim 14, wherein the membrane is substantially non-radiative.

19. The kit of claim 14, wherein the membrane is black.

20. The kit of claim 14, wherein said filtration vessel prevents microorganisms from depositing on the edges of the membrane.

21. The kit of claim 14, wherein the filtration vessel further comprises an access area to allow manipulation of the edge of the membrane.

22. The kit of claim 14, wherein said growth medium is proud.

23. The kit of claim 14, wherein said growth medium retains flatness as it dries.

24. The kit of claim 14, wherein said radiative component comprises radiative plastic or growth medium.

25. The kit of claim 24, wherein said radiative plastic or growth medium is imaged via a through hole in said rim.

26. The kit of claim 14, wherein said radiative component comprises printed or embossed fluorescent material.

27. The kit of claim 14 wherein said radiative component comprises radiative growth medium.

28. A kit for detecting microorganisms, comprising the device of claim 1, together with a membrane adapted to be placed over the growth medium such that microorganisms deposited on the membrane receive nourishment from said medium.

29. The kit of claim 28, wherein the membrane is substantially non-radiative.

30. The kit of claim 28, wherein the membrane is black.

31. The kit of claim 28, wherein said growth medium is proud.

32. The kit of claim 28, wherein said growth medium retains flatness as it dries.

33. The kit of claim 28, wherein said radiative component comprises radiative plastic or growth medium.

34. The kit of claim 33, wherein said radiative plastic or growth medium is imaged via a through hole in said rim.

35. The kit of claim 28, wherein said radiative component comprises printed or embossed fluorescent material.

36. The kit of claim 28, wherein said radiative component comprises radiative growth medium.

* * * * *